United States Patent [19]

Lovalenti

[11] Patent Number: 4,584,469
[45] Date of Patent: Apr. 22, 1986

[54] OPTICAL DETECTION OF RADIAL REFLECTIVE DEFECTS

[75] Inventor: Sam Lovalenti, Toledo, Ohio
[73] Assignee: Owens-Illinois, Inc., Toledo, Ohio
[21] Appl. No.: 454,512
[22] Filed: Dec. 30, 1982
[51] Int. Cl.⁴ ............................................. G01N 9/04
[52] U.S. Cl. ................................ 250/223 B; 356/240
[58] Field of Search ........................... 250/223 B, 224; 356/240; 209/526

[56] References Cited

U.S. PATENT DOCUMENTS

| | | | |
|---|---|---|---|
| 3,171,033 | 2/1965 | Mathias | 250/223 B |
| 3,974,378 | 8/1976 | Brugger | 250/223 B |
| 4,136,930 | 1/1979 | Gomm et al. | 250/223 B |
| 4,171,481 | 10/1979 | Mima et al. | 250/223 B |
| 4,280,624 | 7/1981 | Ford | 250/223 B |
| 4,338,028 | 7/1982 | Tailleur et al. | 250/223 B |
| 4,467,350 | 8/1984 | Miller | 250/223 B |

Primary Examiner—David C. Nelms
Assistant Examiner—J. Gatto
Attorney, Agent, or Firm—John R. Nelson

[57] ABSTRACT

A method and apparatus for inspecting a translucent container to detect a radial reflective defect in the container is disclosed. The apparatus comprises means for illuminating a container by focusing a radiant beam of light into an elongated image extending in a direction parallel to the longitudinal axis of the container along a portion of the container being inspected. The apparatus also comprises means focused on the illuminated portion of the container for sensing the intensity of light reflected from the illuminated portion and for viewing the illuminated portion from a direction and forming an angle ranging from about 75 degrees to about 105 degrees from a path of the incident beam of light. The sensing means provides a plurality of the electrical signals each proportional to the reflected intensity from a corresponding position on the illuminated portion of the container. The apparatus also comprises means responsive to the plurality of electrical signals for providing a reject signal when one of the plurality of electrical signals exceeds a predetermined threshold in response to the presence of a reflective defect.

14 Claims, 4 Drawing Figures

OPTICAL DETECTION OF RADIAL REFLECTIVE DEFECTS

FIELD OF THE INVENTION

This invention relates to inspecting a translucent container to detect a radial reflective defect in the container and, more particularly, to a method and apparatus therefor.

BACKGROUND OF THE INVENTION

Glass containers are typically formed by forcing gas into the interior of a parison of semimolten glass in a mold. The glass parison expands against the interior surfaces of the mold to form a bottom and a sidewall with an annular rim defining an opening of the container. During the forming process, various types of defects may be formed, some of which require the container to be rejected. Defects known as split seams and vertical checks may be present in the sidewall of the container and may extend through the entire thickness of the sidewall so that it weakens the container to the extent that it may leak or even shatter during filling, sealing or subsequent handling. Split seams and vertical checks are mirror-like or reflective cracks that lie in a longitudinal plane parallel to the longitudinal axis of the container and extend generally radially from the longitudinal axis of the container. For convenience, the split seam defect and the vertical check defect will be referred to generically as radial reflective defects.

An inspection device for detecting a radial reflective defect or crizzle is disclosed in U.S. Pat. No. 3,171,033 to B. B. Mathias et al and assigned to the assignee of the present invention. In this inspection device, a beam of radiant energy which can be transmitted through the material of the container is focused on a singular spot on the interior wall of the rim of the container at an acute angle to a radial plane. A radial reflective defect will cause a portion of the beam to be reflected by the reflective surface of the defect while the other portion of the beam is refracted. An element sensitive to the radiant energy of the beam is positioned with its line of vision forming an angle of 75 degrees to 105 degrees with the direction of the beam toward the rim so that the sensitive element will become energized by the passage of a radial reflective defect into the path of the singular spot of the beam. Means are provided in the line of vision of the sensitive element for focusing the portion of the beam directed into the element in a plane adjacent the element. When the sensitive element becomes energized, it provides a signal which actuates a mechanism to reject the container. The major problem unsolved by this previous invention relates to the limitations associated with using a single spot illumination to detect radial reflective defects. The single spot illuminates only the rim portion of the container and therefore is capable of detecting only those radial defects in the rim. However, radial defects may be formed anywhere along the sidewall of the container. U.S. Pat. No. 4,171,481 granted Oct. 16, 1979, to Y. M. Mima et al, discloses an inspection device which also employs a beam of radiant energy, but which also comprises a multisurface rotary mirror which reflects the beam to longitudinally scan the sidewall of the container as it rotates. The device also comprises a pair of eliptical cylindrical mirrors to gather and focus the light on an array of photoelectric elements. Although this device does scan the sidewall of the container, the mirrors required to implement the scanning are complex in shape and difficult to maintain in a dirty operational environment.

SUMMARY OF THE INVENTION

The present invention is directed to a method and apparatus for inspecting a translucent container to detect a radial reflective defect in the container and for rejecting the container in response to a reject signal indicating the presence of a reflective defect. The apparatus comprises means for illuminating the container by focusing a radiant beam of light to form an elongated image extending in a direction parallel to the longitudinal axis of the container along and of a length sufficient to cover that portion of the container wall being inspected. The beam is focused against the interior wall surface and intercepts the surface at an acute angle to a vertical radial plane extending through the illuminated interior wall portion of the container. The apparatus also comprises light sensing means in the form of a linear array camera focused on the illuminated portion of the container for sensing the intensity of light reflected from the illuminated portion and is positioned to view the illuminated portion from a direction forming an included angle ranging from 75 degrees to 105 degrees from the path of the incident beam of light. The camera output is in the form of a plurality of electrical signals each proportional to the reflected intensity from a corresponding position or point on the illuminated portion of the container wall. The apparatus also comprises means responsive to the plurality of electrical signals by providing a reject signal when one of the plurality of electrical signals exceeds a predetermined threshold in response to the presence of a reflective defect.

Rather than using a complicated mirror arrangement, the illuminating means of the instant invention comprises a source of light and a cyclindrical lens disposed between the source and the container to form the elongated image extending generally to the longitudinal axis of the container. Furthermore, the sensing means of the apparatus comprises a plurality of the photosensitive devices or pixels to provide the electrical signals and a lens disposed between the pixels and the container which focuses points along the illuminated portion of the container wall on the plurality of pixels. Therefore, the instant invention inspects an entire longitudinal dimension of the container to detect radial reflective defects as the container rotates without the complex and sensitive mirror system described above.

DETAILED DESCRIPTION OF THE INVENTION

Figures 1, 2:
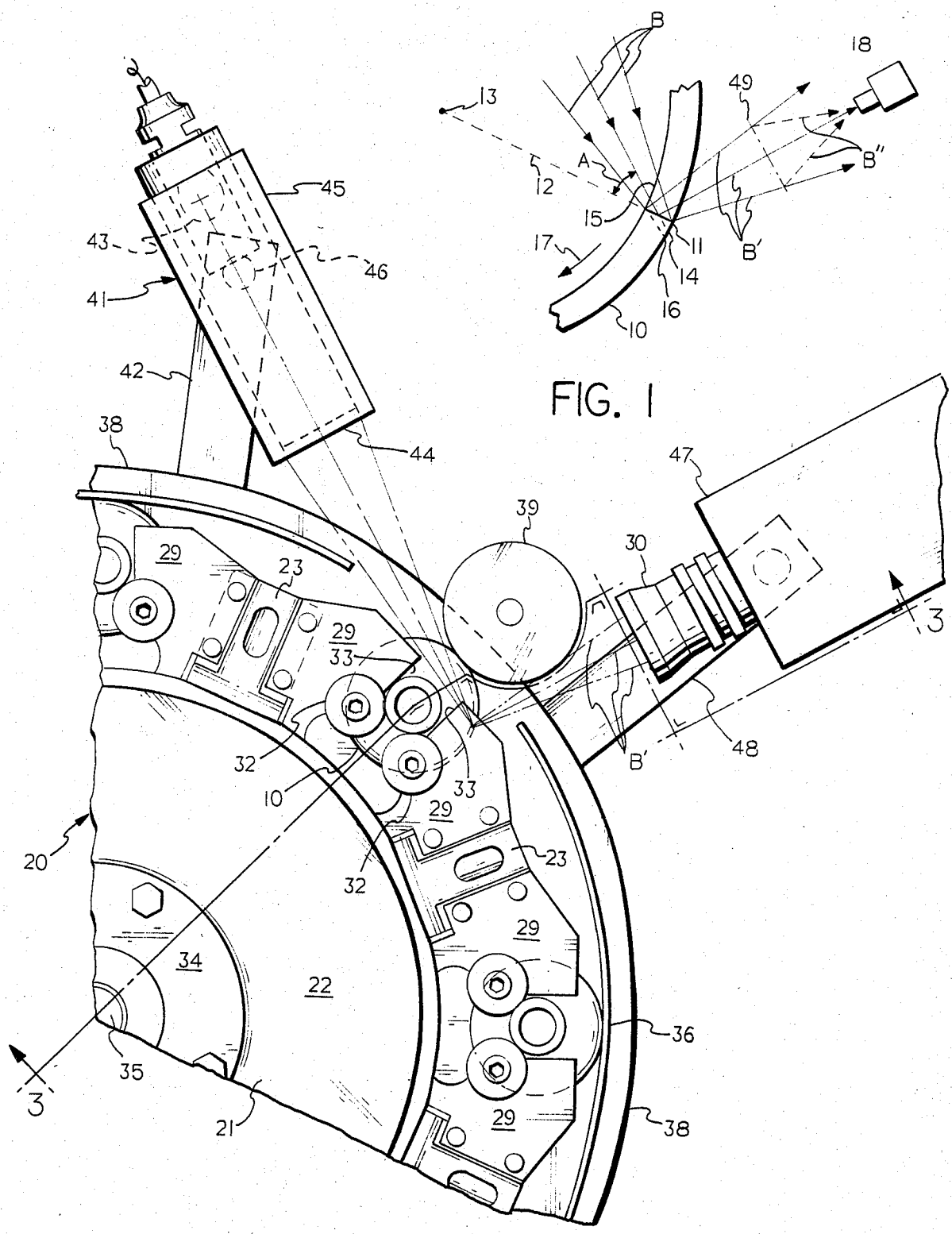
FIG. 1 is a horizontal section, breakaway view of a glass container and a camera for detecting a radial reflective defect in the glass container according to the invention.
FIG. 2 is a plan view of a light source and a camera mounted on an inspection device for detecting radial reflective defects in a container according to the invention.

Referring to FIG. 1, a horizontal section, breakaway view of a glass container 10 containing a radial reflective defect 11, hereinafter referred to as the RR defect 11, is shown. The RR defect 11 is a mirror-like reflective crack that lies in a longitudinal plane 12 generally parallel to the longitudinal axis 13 of the container 10 and extends generally radially from the longitudinal axis 13 of the container 10. The container 10 is illuminated by focusing a radiant beam of light B to form an elongated image extending in a direction running generally parallel to the longitudinal axis 13 of the container 10 along a portion 14 of the container 10 being inspected. The beam B is directed against the interior surface 15 of the illuminated portion 14 of the container 10 and exits through the exterior surface 16 of the illuminated portion 14. Hence the elongated image illuminating the container 10 is bounded in the horizontal plane by the beam B, itself, and the interior and exterior surfaces 15 and 16, respectively, of the illuminated portion 14 of the container 10.

The beam B is directed against the interior surface 15 in a direction forming an acute angle A to the vertical, radial plane 12. The acute angle A is between 40 degrees and 50 degrees, but preferably 45 degrees as disclosed in U.S. Pat. No. 3,171,033 granted to B. B. Mathias et al, assigned to the assignee of the present invention, and hereby incorporated by reference. As the container 10 is rotated about the longitudinal axis 13 in a direction indicated by arrow 17 causing the RR defect 11 to enter the path of the beam B, the RR defect 11 reflects a portion B' of the beam B at an angle between 80 degrees and 100 degrees; the RR defect 11 reflects the beam B at an angle of about 90 degrees if the acute angle A is about 45 degrees. Means 18 focused on the illuminated portion 14 of the container 10 for sensing the intensity of the reflected light beam B' is positioned to view the illuminated portion 14 of the container 10 at an angle ranging from 75 degrees to 105 degrees from the path of the incident beam of light B as disclosed in U.S. Pat. No. 3,171,033.

Figure 3:
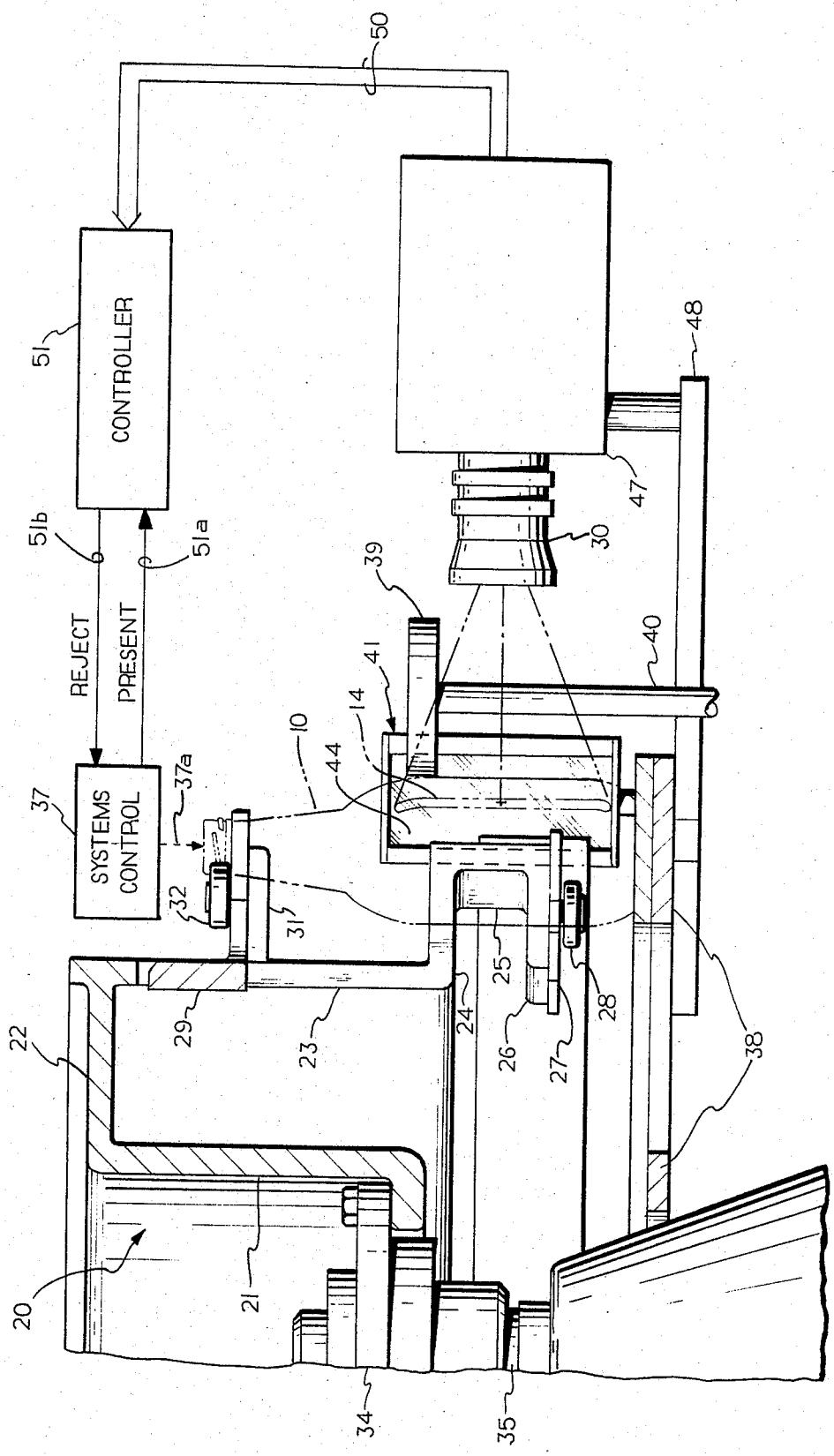
FIG. 3 is a cross-sectional view of the apparatus shown in FIG. 2 taken along the line 3—3 and a controller for providing a reject signal in response to a detected reflective defect in accordance with the invention.

The container 10 is handled by a bottle inspection system disclosed in U.S. Pat. No. 3,313,409, granted to J. R. Johnson, assigned to the assignee of the present invention and hereby incorporated by reference. A portion of the inspection system is shown in FIGS. 2 and 3 and comprises a star wheel indicated generally at 20 which is formed by a generally cylindrical hub 21 having a portion 22 extending radially outwardly therefrom to which downwardly extending arms 23 are attached and spaced at intervals about the periphery of the horizontally extending portion 22 of the hub 21. The downwardly extending arms 23 are provided with horizontally extending ledges 24 which extend radially outwardly to a point at which a downwardly extending arm extension 25 is connected. The downwardly extending extension 25 in turn has an inwardly extending horizontal ledge 26 formed thereto. The inwardly extending ledges 26 on the arms 23 serve as mounts for plates 27 which are attached to the lower surface thereof. Each plate 27 extends horizontally outward from the sides of the ledge 26 to which it is attached and each plate 27 carries a pair of bottle engaging rollers 28. Plates 29 extend between adjacent arms 23. Each arm 23 is provided with an angle bracket 31 which may be adjustably clamped to the arm 23 by suitable fasteners.

Each plate 29 carries a pair of rollers 32 which are adapted to engage the finish or threaded neck portion of the glass container 10. The container 10 is shown in phantom line in FIG. 3 and in full line in FIG. 2. The adjacent plates 29 define a space 33 therebetween which is sufficiently large to receive the neck of the container 10. The two neck-engaging rollers 32 are mounted toward the rear portion of the space 33 and are equidistant from a plane passing through the center of the hub 21 and the center of the container 10.

The hub 21 is connected to a circular plate 34 which in turn is fastened to the upper end of a drive shaft 35. The drive shaft 35 is connected to a suitable indexing drive (not shown) which turns the drive shaft 35 and the star wheel 20 connected thereto. The star wheel 20 carries the container 10 which has been positioned in the confines or "pocket" of the star wheel 20 to successive inspection stations. In this fashion, containers are moved through a series of inspection stations, only one of which is of specific concern in the present invention as indicated in detail in FIG. 3. As the containers are moved through the plurality of inspection stations, they are held within the confines of the pockets in the star wheel 20 by side-engaging rails 36 that are at a height which will render the containers fairly stable as they are moved. There is also a disposal station (not shown) at which defective containers may be rejected as disclosed in U.S. Pat. No. 3,313,409. The star wheel 20 carries the defective container to the exit station at which a plunger actuated by a cylinder connected thereto is positioned to prevent the defective container from leaving the star wheel 20 in advance of the disposal or reject station. This cylinder is actuated by an electrical signal provided by a systems control box 37 associated with the bottle inspection system as indicated by a dashed line 37a. As the containers moved around from station to station, there bottoms slide on a stationary surface supported by a horizontal, generally circular table 38. The side rails 36 are interrupted just in advance of the station where the inspection is being carried out. When the container 10 is at the designated inspection station, it is rotated about its longitudinal axis 13 through at least 360 degrees of rotation. Rotation of the container 10 about its axis 13 is accomplished by a wheel 39 which has a friction surface, such as a rubber tread. The wheel 39 is mounted on the upper end of a vertical shaft 40, the lower end of which is ultimately driven by the drive (not shown) associated with the bottle inspection system. The shaft 40 and the wheel 39 are biased in the direction of the axis 13 of the container 10 in a yieldingly manner so that when indexing of the star wheel 20 takes place, the shoulder of the container 10 may pass from engagement with the wheel 39 without undue stress. However, it is necessary that the surface of the wheel 39 engage the shoulder of the container 10 with sufficient force to assure rotation of the container 10 about its longitudinal axis 13.

Illuminating means indicated generally at 41 is supported by a bracket 42 mounted on the circular table 38 to illuminate the container 10. The illuminating means 41 comprises a source of light 43 or incandescent light bulb and a cylindrical lens 44 disposed between the source 43 and the container 10 so that the lens 44 focuses the light from the source 43 to form the elongated image 14 along the cylindrical wall of the container 10. In the preferred embodiment, the filiment of the incandescent light bulb 43 is oriented longitudinally in alignment with the longitudinal axis of the cylindrical lens 44. The source of light 43 and the cylindrical lens 44 are both mounted in a housing 45 which is supported by the bracket 42. An aperture 46 can be positioned between the light source 43 and the cylindrical lens 44 so that the light from the source 43 diverges to uniformly illuminate the flat surface of the cylindrical lens 44. The elongated image of light 14 extends in a direction running generally parallel to the longitudinal axis 13 of the container 10 as illustrated more specifically in FIG. 3. The elongated image of light 14 is viewable by the sensing means 18 which can be, for example, a solid state camera 47 focused on the elongated image or illuminated portion 14 of the container 10 as shown in FIG. 3 to sense the intensity of the reflected light beam B' as shown in FIGS. 1 and 2. The camera 47 is mounted on a bracket 48 supported by the circular table 38. The camera can be, for example, the LC110 Line Scan Camera manufactured by Reticon located in Sunnyvale, Calif., which contains a linear array of 256 light sensitive diodes or pixels (not shown) and a lens 30 disposed between the linear array and the container 10 for focusing the array to view the elongated image 14. The linear array is aligned in parallel with the longitudinal axis 13 of the container 10 so that the pixels in the array provide a plurality of electrical signals each proportional to the reflected intensity from a corresponding position along the elongated image 14 on the container 10. The elongated image 14 is focused on the pixels by the lens 30 in the camera 47 disposed between the pixels and the container 10. Therefore, as the wheel 39 rotates the container 10 while the pixels are viewing the elongated image 14, the instant invention inspects the entire sidewall of the container 10 to detect RR defects. To further increase the sensitivity of the camera 47, a second cyclindrical lens 49 can be positioned between the container 10 and the camera 47 to gather more of the reflected light beam B' from a RR defect 11 in the elongated image 14 as illustrated by the dashed lines B" in FIG. 1.

The instant invention also comprises a controller 51 that is responsive to the plurality of electrical signals provided by the pixels in the camera 47 along the wires in a bus 50. In operation, the systems control 37 provides the controller with a signal along wires 51a indicating that the container 10 is present at the inspection station and ready to be inspected. If an RR defect is present, one of the plurality of electrical signals provided by the pixels of the camera 47 will exceed a predetermined threshold causing the controller 51 to provide a reject signal to the systems control 37 along a wire 51b. The systems control 37 responds by causing the plunger to prevent the defective container from leaving the starwheel in advance of the disposal station as described above.

Figure 4:
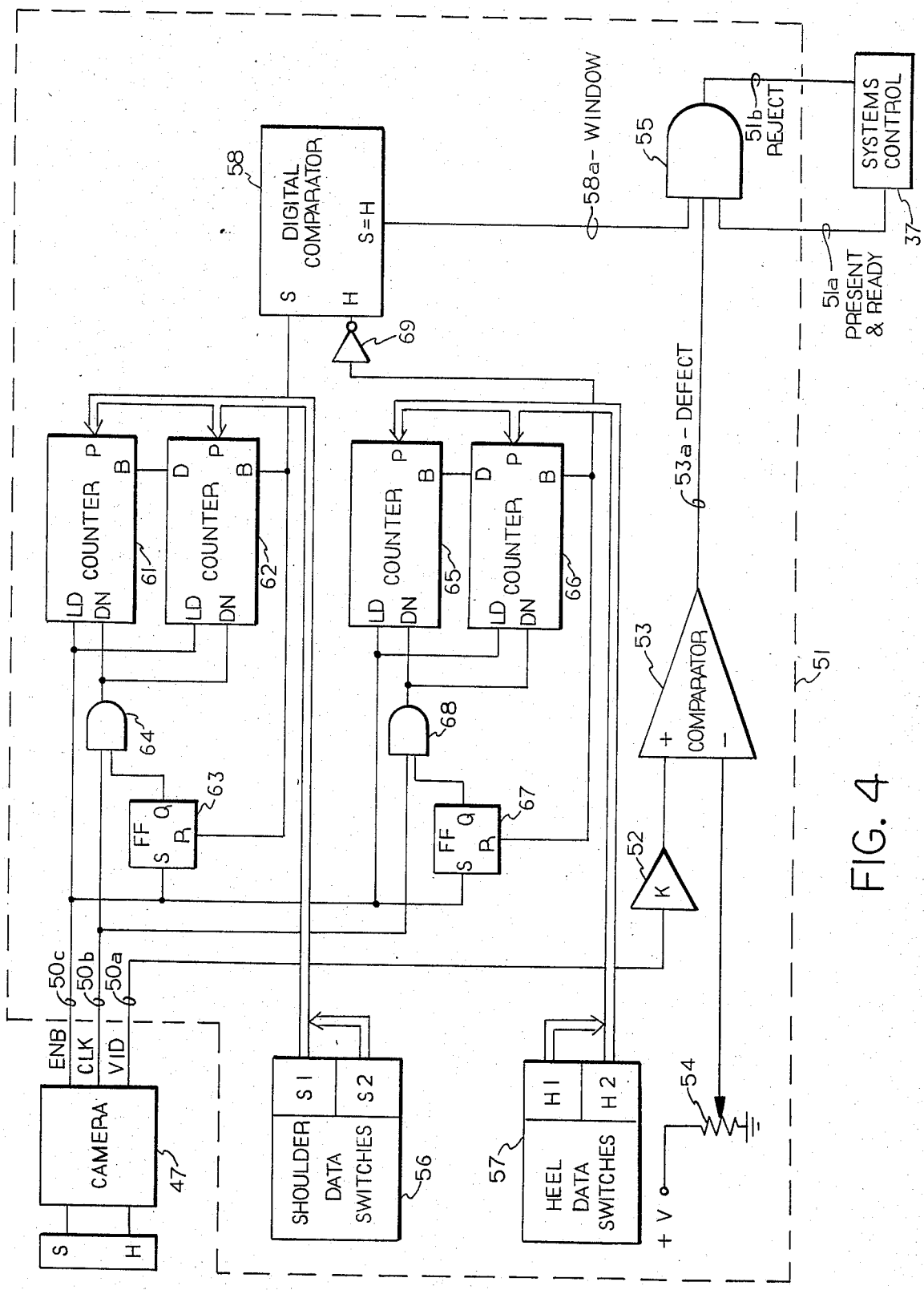
FIG. 4 is an electrical schematic of the controller shown in FIG. 3 in accordance with the invention.

A detailed electrical schematic of the controller is shown in FIG. 4. The wires 50 connecting the camera 47 to the controller 51 comprise a wire 50a for providing the plurality of electrical signals from the pixels or the video signal VID, a wire 50b for providing a clock signal CLK representing the rate at which the individual pixels of the camera 47 are interrogated, and a wire 50c providing an enable signal ENB indicating the starting of the interrogation of the pixels of the camera 47. The wire 50a providing the video signal VID is connected to the input of an amplifier 52, the output of which is connected to the noninverting input of a comparator 53. The inverting input of the comparator 53 is connected to the wiper terminal of a grounded variable resistor 54, the other terminal of which is connected to a source of positive voltage V. The output of the comparator 53 is connected by a wire 53a to the first input of a three-input AND gate 55, the output from which provides the reject signal along the wire 51b to the systems control 37. The wires 51a from the system control 37 is connected to the second input of the AND gate 55 to indicate whether the container 10 is at the appropriate station ready to be inspected. Assuming for ease of explanation that the AND gate 55 is a two-input gate, 53a and 51a, a reject signal would be generated if a defect is present as indicated by a high signal at 53a when the container 10 is at the appropriate station ready for inspection as indicated by a high signal at 51a. A defect signal is provided by the comparator 53 at 53a when any one of the plurality of electrical signals provided by the pixels of the camera 47 exceeds a predetermined threshold as set by the variable resistor 54 in response to the presence of a RR defect 11.

Although the pixels of the camera 47 are focused to view the entire length of the elongated image 14, the controller 51 (FIG. 3 and 4) also comprises circuitry to limit the data gathered during inspection of the container 10. In other words, only a "window" of data from intermediate pixels with respect to a corresponding portion of the container 10 which needs to be inspected may be of interest. Referring back to FIG. 3 for an example, it may be desirable to ignore the upper curved portion of the elongated image 14 associated with the curvature of the shoulder of the container 10, as well as the lower curved portion of the elongated image 14 associated with the curvature of the heel of the container 10. In such case, and again referring to FIG. 4, an operator will set a bank of data switches 56 for the shoulder of the container 10 to a number S indicating at what pixel inspection should begin and a bank of data switches 57 for the heel of the container 10 to a number H indicating at what pixel number inspection should end. When the intermediate pixels between the starting and stopping pixels, S and H respectively in the camera 47, set by the data switches 56 and 57, respectively, are being interrogated by the electronics of the camera 47, the inputs S and H of a digital comparator 58 are both high so that the equality output, S=H, of the comparator 58 provides a high signal or a window signal to the third input 58a of the AND gate 55. Therefore, a reject signal is provided by the AND gate 55 only for those defect signals from the comparator 53 occuring within the window being inspected as determined by the digital comparator 58.

The circuitry for setting the starting pixel S comprises the data switches 56, counters 61 and 62 preset by corresponding banks of data switches S1 and S2 at the preset terminals P thereof, and control logic including a flip-flop 63 and an AND gate 64. Although two banks of data switches S1 and S2 for the corresponding two counters 61 and 62 are shown, any number of counters can be used for a setting the starting pixel as required. The enable signal ENB provided along the wire 50c is provided to the load terminals LD of the counters 51 and 62 as well as to the set input S of the flip-flop 63. The Q output of the flip-flop 63 is connected to an input of the AND gate 64, the output of which is connected to the down-counting inputs DN of the counters 61 and 62. The clock signal CLK is provided along the wire 50b to the other input of the AND gate 64. The borrow output B of the counter 61 is connected to the down input D of the counter 62. The borrow output B of the counter 62 is connected to the S input of the digital comparator 58 and the reset terminal R of the flip-flop 63. In operation, an enable signal ENB from the camera 47 causes both of the counters 61 and 62 to be loaded by the numbers preset by the banks of data switches S1 and S2. The enable signal ENB also sets the flip-flop 63 which gates the clock pulses CLK to the counters 61 and 62 which begin counting down to zero from the present number S representing the starting pixel. When the counters both reach zero, the counter 62 causes a high signal to be provided to the normally-low S input of the digital comparator 58 and resets the flip-flop 63 in preparation for the inspection of the next container. The high signal at the S input of the digital comparator 58 indicates that scanning of the intermediate pixels of interest in the "windows" has begun.

The portion of the electronic circuit for setting the stopping pixel H comprises the data switches 57, counters 65 and 66 preset by corresponding banks of data switches H1 and H2 at the preset terminals P thereof, and control logic including a flip-flop 67 and an AND gate 68. This circuitry functions in the same manner as does the above described circuit for setting the starting pixel S. However, the borrow output B of the counter 66 is connected to the H input of the digital comparator 58 through an inverter 69 so that the H input is normally high. Therefore, when the normally-low S input of the digital comparator 58 goes high, the equality output, S=H, thereof provides a high signal to the AND gate 55 indicating that the inspection window is open. When the counters 65 and 66 reach zero after counting down from the preset number H corresponding to the number of the stopping pixel, the borrow output B of the counter 66 goes high causing the signal at the H input of the digital comparator 58 to go low. Thus, the inequality causes the equality output, S=H, to go low providing an indication to the AND gate 55 that the inspection window is closed. In such case, the AND gate 55 is inhibited from providing a reject signal in response to a defect signal from the comparator 53.

The foregoing disclosure is the best mode devised by the inventor for practicing this invention. It is apparent, however, to one skilled in the pertinent art that various changes may be made in details of construction from those shown in the attached drawings and discussed in conjunction therewith without departing from the spirit and scope of this invention. For example, the shoulder as well as the cylindrical walls of the container 10 can be inspected according to the invention by shaping the elongated image 14 with a mask to also illuminate the shoulder and by correspondingly shaping the linear array, or using a matrix array, to view the contoured elongated image 14. The detail in the foregoing disclosure is intended to enable one skilled in the pertinent art to practice the instant invention. Therefore, it is to be understood that this invention is not to be limited to the specific details shown and described.

What I claim is:

1. Apparatus for inspecting a translucent container to detect a radial reflective defect in the container and for rejecting the container in response to a reject signal indicating the presence of a reflective defect, said apparatus comprising:

means for illuminating the container by focusing a radiant beam of light to form a narrow elongated image extending in a direction parallel to the longitudinal axis of the container along a sidewall portion of the translucent container being inspected and directing said beam against the interior surface of said illuminated wall portion in a direction forming an acute angle to a radial plane extending through and parallel to said illuminated portion of the container;

camera means focused on the exterior of said illuminated portion of the container wall for sensing the intensity of light reflected from said illuminated portion, said camera means viewing the illuminated portion from a direction forming an angle ranging from between 75 degrees to 105 degrees from the path of said beam of light, said reflected light intensity sensing camera means providing a plurality of electrical signals each proportional to the intensity of reflected light from a corresponding position on said illuminated wall portion of the container; and, means responsive to said plurality of electrical signals for providing a reject signal when one of said plurality of electrical signals exceeds a predetermined threshold in response to the presence of a reflective defect.

2. Apparatus as recited in claim 1 also having a drive mechanism for rotating the container at least 360 degrees and wherein said light sensing camera means provides sequential sets of said plurality of electrical signals as the container is inspected for radial reflective defects.

3. Apparatus as recited in claim 1 wherein said acute angle is between 40 and 50 degrees.

4. Apparatus as recited in claim 1 wherein said means for illuminating said container comprises a source of light and a cylindrical lens disposed between said source and the container so that said lens focuses the light from said source to form said elongated image along the cylindrical wall of the container.

5. Apparatus as recited in claim 1 wherein said light sensing camera means comprises a plurality of pixels each providing one of said plurality of electrical signals and a lens disposed between said pixels and the container so that said lens focuses said illuminated portion of the container along said plurality of pixels.

6. Apparatus as recited in claim 5 further comprising a cylindrical lens disposed between said camera lens and the container so that said lens gathers more of the light reflected from said illuminated portion of the container for focusing on said plurality of pixels.

7. Apparatus as recited in claim 1 wherein said reject signal providing means comprises an amplifier having an input responsive to said plurality of electrical signals, a comparator having a noninverting input connected to the output of said amplifier and an inverting input connected to an adjustable source of positive voltage for providing a predetermined threshold to the inverting input of said comparator, the output of said comparator providing said reject signal when one of said amplified electrical signals exceeds said predetermined threshold.

8. Apparatus as recited in claim 5 further comprising means responsive to said light sensing camera means for enabling said reject signal when one of a portion of said plurality of electrical signals exceeds said predetermined threshold.

9. Apparatus as recited in claim 8 wherein said light sensing camera means sequentially interrogates said plurality of pixels to provide said plurality of electrical signals in sequence and provides a clock signal synchronous therewith and wherein said enabling means comprises an AND gate having a first input connected to the output of said comparator and a second input connected to an equality output of a magnitude comparator having two inputs, a first counting means responsive to said clock signal for providing a first signal in one binary state to a first input of said magnitude comparator after a first predetermined number of clock pulses, and second counting means responsive to said clock signal for providing a second signal in the other binary state to a second input of said magnitude comparator after a second predetermined number of clock pulses greater than said first predetermined number, whereby the equality output of said magnitude comparator enables said reject signal at the output of said AND gate when the tally of said clock pulses is between said first and second predetermined number of clock pulses.

10. A method for inspecting a translucent container to detect a radial reflective defect in the container sidewall and for rejecting the container in response to a reject signal indicating the presence of a reflective defect comprising the steps of:

illuminating the container by focusing a radiant beam of light to form an elongated image extending in a direction running parallel to the longitudinal axis of the container along a portion of the container sidewall being inspected;

directing the beam against the interior surface of the illuminated portion in a direction forming an acute angle with respect to a radial plane extending through and parallel to the illuminated portion of the container;

sensing light reflected from the illuminated portion in a direction at an angle ranging from 75 degrees to 105 degrees from the path of the incident beam of light;

providing a plurality of electrical signals with each signal being proportional to the intensity of light reflected from a corresponding position on the illuminated portion of the container; and, providing a reject signal when one of the plurality of electrical signals exceeds a predetermined threshold indicating the presence of a reflective defect.

11. A method as recited in claim 10 further comprising the steps of rotating the container at least 360 degrees while being inspected and providing sequential sets of the plurality of electrical signals as the container is being rotated so that the entire sidewall of the container is inspected for radial reflective defects.

12. A method as recited in claim 10 wherein the beam is directed against the surface of the illuminated portion in a direction forming an acute angle between 40 and 50 degrees to the radial plane.

13. A method as recited in claim 10 further comprising the step of enabling the reject signal only when one of the plurality of electrical signals which corresponds to a preselected portion of the image being viewed exceeds the predetermined threshold.

14. In a system for inspecting the entire sidewall of a translucent container to detect a radial reflective defect in the container sidewall while rotating said container through at least 360 degrees and for rejecting the container in response to a reject signal indicating the presence of a reflective defect, apparatus comprising:

a light source;

means for focusing said light source into a narrow beam of light to form an elongated, illuminated image extending in a direction running parallel to the longitudinal axis of the container along the sidewall of the container being inspected, said beam being directed against the interior surface of said sidewall in a direction forming an acute angle with respect to a radial plane extending through and parallel to said illuminated image on the container sidewall;

camera means for sensing the intensity of light reflected from said illuminated image, said camera viewing the illuminated image from a direction forming an angle ranging from 75 degrees to 105 degrees from the path of said beam of light, said camera means providing as plurality of electrical signals each proportional to the reflected light intensity from a corresponding position on said illuminated image of the container sidewall; and, comparison means connected to said of electrical signals and a threshold signal for providing a reject signal when one of said plurality of electrical signals exceeds a predetermined threshold in response to the presence of a reflective defect.

* * * * *

UNITED STATES PATENT AND TRADEMARK OFFICE
CERTIFICATE OF CORRECTION

PATENT NO. : 4,584,469
DATED : April 22, 1986
INVENTOR(S) : Sam Lovalenti

It is certified that error appears in the above-identified patent and that said Letters Patent are hereby corrected as shown below:

Column 10, Claim 14, line 38, after "said" insert --plurality--

Signed and Sealed this

Twenty-fifth Day of November, 1986

Attest:

DONALD J. QUIGG

*Attesting Officer*     *Commissioner of Patents and Trademarks*